United States Patent [19]

Komatsu

[11] Patent Number: 4,778,387
[45] Date of Patent: Oct. 18, 1988

[54] GUIDE ATTACHMENT FOR DENTAL TREATMENT TIP

[75] Inventor: Hiroyuki Komatsu, 3-14-14, Higashi, Shibuya-ku, Tokyo, Japan

[73] Assignee: Hiroyuki Komatsu, Tokyo, Japan

[21] Appl. No.: 19,028

[22] Filed: Feb. 26, 1987

[30] Foreign Application Priority Data

Mar. 3, 1986 [JP] Japan .................. 61-43947

[51] Int. Cl.$^4$ .................................................. A61C 1/16
[52] U.S. Cl. .................................................. 433/116
[58] Field of Search .......................... 433/116, 75, 76

[56] References Cited

U.S. PATENT DOCUMENTS

| 525,278 | 8/1894 | Peck | 433/116 |
|---|---|---|---|
| 594,952 | 12/1987 | Hoyer | 433/116 |
| 1,004,118 | 9/1911 | Waters | 433/116 |
| 1,101,947 | 6/1914 | Morgan | 433/116 |
| 1,216,311 | 2/1917 | Hartman | 433/116 |
| 1,285,273 | 11/1918 | Luzzi | 433/116 |
| 2,238,304 | 4/1941 | Belanger | 433/125 |
| 2,671,269 | 3/1954 | Francis | 433/116 |
| 3,786,566 | 1/1974 | Jelicic et al. | 433/116 |
| 4,571,183 | 2/1986 | Nash | 433/116 |

FOREIGN PATENT DOCUMENTS 0602086 7/1978 Switzerland .................. 433/116

Primary Examiner—John J. Wilson
Assistant Examiner—Adriene J. Lepiane
Attorney, Agent, or Firm—Limbach, Limbach & Sutton

[57] ABSTRACT

A guide attachment for guiding a dental treatment tip such as a dental bur is provided. The guide attachment is composed of a guide member for guiding the dental treatment tip and a fixing member for mounting the guide member to a dental handpiece in which the dental treatment tip is accommodated.

11 Claims, 2 Drawing Sheets

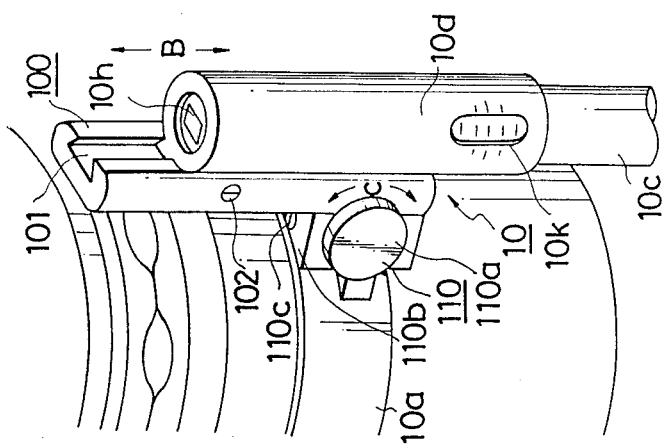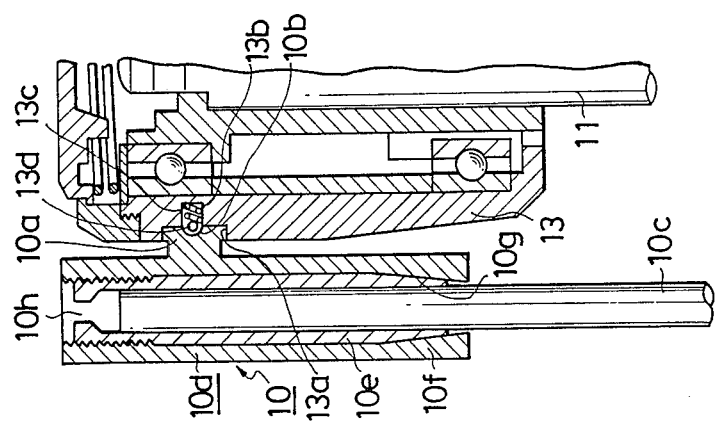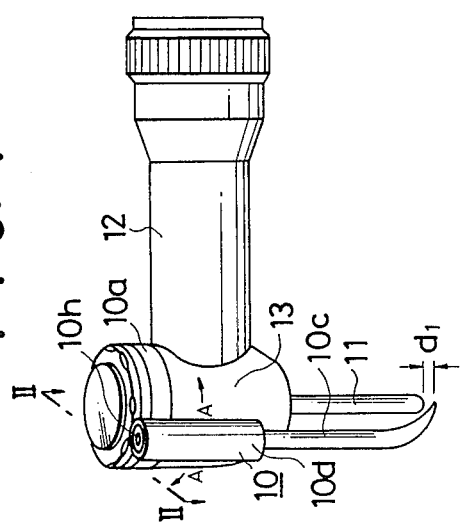

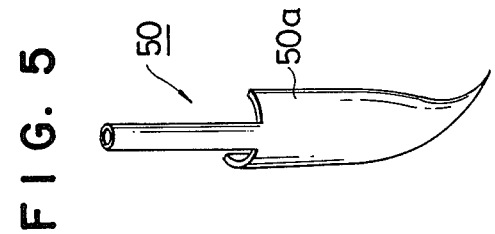
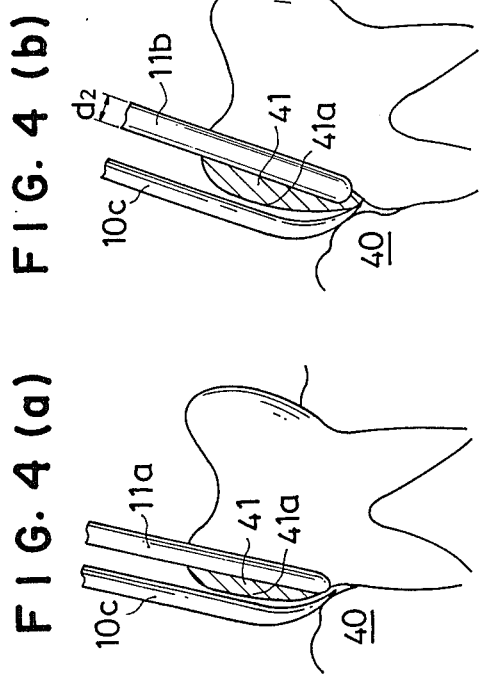
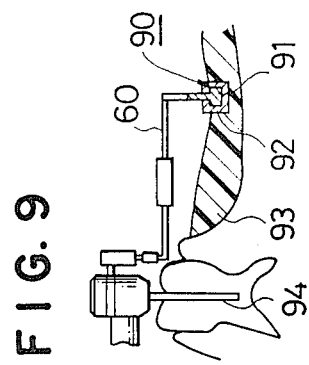
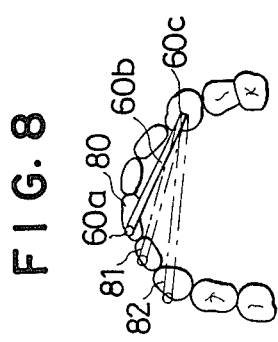
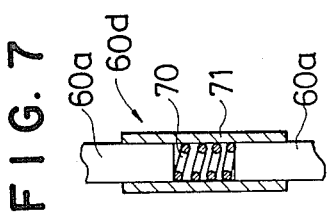
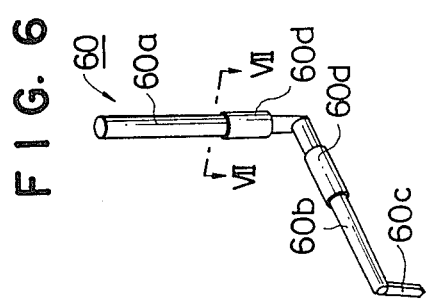

4,778,387

GUIDE ATTACHMENT FOR DENTAL TREATMENT TIP

BACKGROUND OF THE INVENTION

1. Field of the Invention

This invention relates to a guide attachment for guiding a dental treatment tip such as a dental bur.

2. Related Art Statement

Heretofore, when cutting or grinding teeth for dental treatment or processing, a dental handpiece is used which is equipped with a dental processing tip such as a dental bur. However, the dental handpiece is extremely difficult to handle and its proper operation depends appreciably on the experience and skill of dentists. As a matter of fact, it is being handled in different fashion by individual dentists.

Above all, in order to cut or grind teeth for coating a dental prosthesis, various cutting or grinding methods have been proposed in the art. However, there are many cases where only highly skilled dentists can perform complex grinding operation while manually holding the dental handpiece with the aid of their fingers.

Nonetheless, there has not been developed a guiding apparatus for properly guiding the dental treatment tip attached to the dental handpiece.

OBJECTS AND SUMMARY OF THE INVENTION

It is therefore a principal object of the present invention to provide a guide attachment for a dental treatment tip by means of which the dental treatment tip can be guided properly so that extremely complicated dental treatment can be performed without necessitating special skill.

It is another object of the present invention to provide a guide attachment for a dental treatment tip which makes it possible to completely eliminate the risk of injuring adjacent teeth, tongue, lips or gingiva.

It is a further object of the present invention to provide a guide attachment for a dental treatment tip which can be produced easily at low costs.

According to the present invention, there is provided a guide attachment for guiding a dental treatment tip to perform dental treatment comprising guide means for guiding the dental treatment tip and mounting means for mounting the guide means to a dental handpiece in which the dental treatment tip is accomodated.

BRIEF DESCRIPTION OF THE DRAWINGS

FIG. 1 is a perspective view showing an embodiment of the guide attachment for a dental treatment tip according to the present invention;

FIG. 2 is a sectional view taken along line II—II of FIG. 1, with part being broken away;

FIG. 3 is an exploded view showing an embodiment of the chuck unit, with part being broken away;

FIGS. 4a and 4b are schematic views each showing cutting or grinding of a tooth with the use of the guide attachment shown in FIG. 1;

FIG. 5 is a perspective view showing a modified guide member;

FIG. 6 is a perspective view showing another modified guide member;

FIG. 7 is a sectional view taken along line VII—VII of FIG. 6, with part being broken away;

FIG. 8 is a schematic plan view showing the operation of grinding teeth with the aid of the guide member shown in FIGS. 6 and 7;

FIG. 9 is a schematic side view showing a further modification of a guide member with part being broken away; and FIG. 10 is a fragmentary perspective view showing another embodiment of the guide attachment for a dental treatment tip according to the present invention.

DESCRIPTION OF THE PREFERRED EMBODIMENTS

Preferred embodiments of a guide attachment for a dental treatment tip according to the present invention are hereafter explained by referring to the accompanying drawings.

Referring to FIG. 1, there is shown a guide attachment 10 adapted to guide the dental treatment tip such as a dental bur 11. The guide attachment 10 has an integral annular member 10a for attachment to a head housing 13 of a dental handpiece 12. The annular member 10a is movable about the outer periphery of the side wall of the head housing 13 in the direction of an arrow mark A in FIG. 1 and can be locked at a desired position on the side wall of the head housing 13.

As shown in detail in FIG. 2, the annular member 10a is received in a mating annular groove 13a on the side wall of the head housing 13. The annular member 10a has a plurality of recesses 10b in which there is received a ball 13d under the bias of a spring 13c disposed in a recess 13b formed in the side wall of the housing 13. In this manner, the guide attachment 10 can be secured at any desired position on the periphery of the head housing 13 by rotating the attachment 10 around the head housing 13.

The guide attachment 10 has a guide member 10c for guiding the dental bur 11 and a chuck unit 10d for receiving and chucking the guide member 10c at a desired longitudinal position of the guide attachment 10. As shown in FIGS. 2 and 3, the chuck unit 10d has a collet 10e for accommodating the guide member 10c and a collet sleeve 10f for threadedly accommodating the collet 10e. The foremost part of the collet sleeve 10f is formed with an inclined cam face 10g. When a wrench (not shown) is inserted into an upper opening 10h of the collet 10f and turned manually, a cam face 10i of the collet 10e having a longitudina slit 10j (FIG. 3) abuts on the cam face 10g of the collet sleeve 10f. The cam face 10i of the collet 10e is tightened in this manner for securing the guide member 10c as the slit 10j is contracted.

In the embodiment shown in FIG. 1, the foremost part of the guide member 10c is extended and terminated at a position proximate to the end of the dental bur 11. The guide member 10c is secured by adjusting the chuck unit 10d with the aid of a shim (not shown) so that a distance $d_1$ is maintained between the foremost point of the dental bur 11 and the corresponding foremost point of the guide member 10c.

The cutting of a tooth with the aid of the bur 11 and the guide attachment 10 shown in FIGS. 1 to 3 is now explained by referring to FIGS. 4a and 4b. FIG. 4a shows the operation of what is called a chamfer type cutting. A dental bur 11a of a relatively small diameter is attached to the handpiece 12 while the foremost part of the guide member 10c is inserted and placed in the vicinity of an edge 40 of gingiva. The overall unit comprised of the bur 11a and the guide member 10c is then actuated for cutting to thereby remove an unnecessary portion 41 of the tooth while the overall unit is moved as required with the foremost part of the guide member 10c disposed in the vicinity of the edge 40 of gingiva and inclined as required for chamfer type cutting. At this time, since the guide member 10c is inserted and placed in the vicinity of the edge 40 so as to extend over a protuberant portion 41a of the tooth, while being inclined as required for performing the aforementioned cutting, there is no risk of injuring adjacent teeth, gingiva or the tongue that are effectively protected by the guide member 10c during the cutting.

FIG. 4b shows the operation of the beveled shoulder type cutting. After the termination of the aforementioned chamfer type cutting, the bur 11a is replaced by another bur 11b of a larger diameter and the cutting is performed with the foremost part of the guide member 10c disposed at a position slightly higher than the position during the preceding chamfer type cutting. In this manner, a shoulder may be formed to a height about one half the diameter $d_2$ of the dental bur 11b.

It should be noted that the guide attachment 10 of the present invention can be applied not only to the cutting types shown in FIGS. 4a or 4b but also to various other types of cutting such as feather edge, knife edge or shoulder cutting.

FIG. 5 shows a modified embodiment of the guide member according to the present invention. In the present embodiment, the guide member 50 has a protective plate 50a which is curved as shown. Since the protective area is extended by the guide member 50, the risk of injuring gingiva, adjacent teeth, lips or tongue by the dental bur 11 is further reduced.

FIG. 6 shows a further modified embodiment of the guide member of the present invention. In the present embodiment, the guide member is in the form of a guide unit 60 comprised of a vertically extending rod 60a, a horizontally extending rod 60b secured to the vertically extending rod 60a and a fixed fulcrum member 60c secured to the horizontally extending rod 60b. In effect, the rods 60a, 60b are composed of two separate sections connected together by length adjustment units 60d, 60d. As shown in FIG. 7, each length adjustment unit 60d is comprised of a spring 70 and a tubular member 71 adapted for slidably accommodating separate sections of the vertically extending member 60a. The provision of the length adjustment unit 60d makes it possible to adjust the length of the guide unit 60 both horizontally and vertically as desired.

In FIG. 8, there is diagrammaticaly shown a cutting method with the aid of the guide unit 60 shown in FIGS. 6 and 7. With the fulcrum member 60c fixed at a given point, teeth 80, 81 and 82 are cut in this order with the aid of the length adjustment units 60d. In this manner, cutting can be performed with one point 60c of the guide unit 60 being fixed. This cutting method is effective inter alia for the application of an artificial crown since the cutting can be effected to provide cutting surfaces of a constant angle.

In a modified embodiment shown in FIG. 9, the fulcrum member 60c shown in FIG. 6 is substituted by a rotary member 90 adapted for rotating the guide unit 60 about a terminal point 91 thereof. The rotary member 90 is in the form of a hollow cylinder opened at the top for rotatably accommodating the terminal point 91. When employing the guide unit 60 shown in FIG. 9, synthetic resin is poured as at 93 in the molten state into the oral cavity and, after the rotary member 90 is previously fixed upright in the resin mass, the resin is cured in situ such that the terminal point 91 of the unit 60 is fixed in position. With the use of the guide unit 60 as described hereinabove, plural holes 94 can be cut so as to be parallel to one another for parallel mounting of sapphire pins (not shown) for securing an artificial tooth (also not shown).

FIG. 10 shows a further modified embodiment of the guide attachment 10 of the present invention. In the present embodiment, a chuck unit 10d is mounted to a longitudinal positioning adjustment unit 100 which is slidable lengthwise of the guide member 10c as indicated by the arrow mark B. The chuck unit 10d is slidably mounted in a trapezoidal groove 101 of the adjustment unit 100 and can be secured at any desired position by a screw 102. In the present modification, a micrometer 10k is provided to the chuck unit 10d for reading out the current position of the guide member 10c.

In the guide attachment 10 shown in FIG. 10, the longitudinal positioning adjustment unit 100 is further provided with an angular positioning adjustment unit 110. The adjustment unit 110 is comprised of a rod 110a and a rotary mounting member 110b which is integral with the longitudinal positioning adjustment unit 100 and which is rotatably mounted with respect to the rod 110a. After setting the desired angular position in the direction shown by the arrow mark C, the screw 110c is tightened for securing. The provision of the adjustment unit 110 makes it possible to make fine adjustment of the angle between the guide member 10c and the dental bur 11.

It is seen from the foregoing that the guide attachment of the present invention provides extremely easy and safe cutting while reducing the load imposed on the dentist so that the dental treatment operations are greatly facilitated.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A guide attachment for guiding a dental treatment tip to perform dental treatment comprising:
   guide means for guiding said dental treatment tip; and
   mounting means for mounting said guide means to a dental handpiece in which said dental treatment tip is accommodated;
   said guide means including a guide member, a chuck unit adapted for accommodating and securing said guide member at a desired longitudinal position, a longitudinal positioning unit associated with said chuck unit so that said chuck unit is adjusted longitudinally along the length of said guide member, and an angular positioning unit for adjusting the angular position of said guide member relative to said dental treatment tip within a plane passing through both the longitudinal centerlines of said dental treatment tip and said guide member.

2. A guide attachment as claimed in claim 1 wherein said guide member extends to and terminates at a position proximate to the foremost point of the dental treatment tip.

3. A guide attachment as claimed in claim 1 or 2 wherein said guide means comprises a protective plate adapted for avoiding damage by said dental treatment tip.

4. A guide attachment as claimed in claim 1 wherein said guide member has length adjustment means.

5. A guide attachment as claimed in claim 4 wherein said length adjustment means comprises a resilient length adjustment member interposed between adjacent sections of the guide member.

6. A guide attachment as claimed in claim 4 wherein a rotary member is provided to a foremost part of said guide member for effecting rotation about said foremost part of said guide member.

7. A guide attachment as claimed in claim 1 wherein said chuck unit comprises a collet for accommodating the guide member and a collet sleeve for accommodating said collet and wherein the guide member is secured at a desired position by moving said collet in said collet sleeve.

8. A guide attachment as claimed in claim 1 wherein said chuck unit comprises a micrometer for measuring the position of said guide member.

9. A guide attachment as claimed in claim 1 wherein said mounting means is mounted to a head housing of the dental handpiece and wherein said mounting means comprises means for rotating and securing said guide means to a desired position around said head housing.

10. A guide attachment as claimed in claim 9 wherein said mounting means comprises an annular member engaged in a mating groove on the side wall of the head housing of the dental handpiece and wherein said means for rotating and securing include first engagement means in said annular member and second engagement means in said head housing.

11. A guide attachment as claimed in claim 10 wherein said first and second engagement means comprise a recess and a ball mounted on a spring.

* * * * *